United States Patent [19]
Granger et al.

[11] Patent Number: 5,811,110
[45] Date of Patent: *Sep. 22, 1998

[54] SKIN CARE COMPOSITIONS CONTAINING FATTY ACID AMIDES AND RETINOL OR RETINYL ESTER

[75] Inventors: Stewart Paton Granger, Paramus; Anthony Vincent Rawlings, Wyckoff; Ian Richard Scott, Allendale, all of N.J.

[73] Assignee: Elizabeth Arden Co., Division of Conopco, Inc., New York, N.Y.

[*] Notice: The term of this patent shall not extend beyond the expiration date of Pat. No. 5,599,548.

[21] Appl. No.: 788,894

[22] Filed: Jan. 22, 1997

Related U.S. Application Data

[63] Continuation of Ser. No. 436,795, May 8, 1995, Pat. No. 5,599,548.

[51] Int. Cl.⁶ .......................... A61K 31/07; A61K 31/16; A61K 7/48
[52] U.S. Cl. .......................... 424/401; 514/725; 514/844; 514/859
[58] Field of Search ........................ 424/401; 514/725, 514/844, 859; 568/378, 824

[56] References Cited

U.S. PATENT DOCUMENTS

| | | | |
|---|---|---|---|
| 3,883,661 | 5/1975 | Young | 424/320 |
| 4,363,815 | 12/1982 | Yu et al. | 424/274 |
| 4,380,549 | 4/1983 | Van Scott et al. | 424/317 |
| 4,857,321 | 8/1989 | Thomas | 424/95 |
| 4,911,928 | 3/1990 | Wallach | 424/450 |
| 5,004,599 | 4/1991 | Scher | 424/61 |
| 5,043,356 | 8/1991 | Fulton, Jr. et al. | 514/549 |
| 5,057,501 | 10/1991 | Thornfeldt | 514/53 |
| 5,093,360 | 3/1992 | Yu et al. | 514/463 |
| 5,124,313 | 6/1992 | Schaeffer et al. | 514/2 |
| 5,216,148 | 6/1993 | Klaus et al. | 540/517 |
| 5,308,551 | 5/1994 | Beauquey et al. | 252/548 |
| 5,492,894 | 2/1996 | Bascom et al. | 514/18 |
| 5,534,265 | 7/1996 | Fowler et al. | 424/489 |
| 5,536,740 | 7/1996 | Granger et al. | 514/392 |
| 5,585,104 | 12/1996 | Ha et al. | 424/401 |
| 5,599,548 | 2/1997 | Granger et al. | 424/401 |
| 5,744,148 | 4/1998 | Habif et al. | 424/401 |
| 5,747,051 | 5/1998 | Granger et al. | 424/401 |
| 5,756,109 | 5/1998 | Burger et al. | 424/401 |
| 5,759,556 | 6/1998 | Burger et al. | 424/401 |

FOREIGN PATENT DOCUMENTS

| | | |
|---|---|---|
| 0 388 275 | 9/1990 | European Pat. Off. . |
| 0 582 458 | 2/1994 | European Pat. Off. . |
| 1126289 | 9/1968 | United Kingdom . |
| WO 93/19743 | 10/1993 | WIPO . |
| WO 93/25177 | 12/1993 | WIPO . |
| WO 94/03156 | 2/1994 | WIPO . |

OTHER PUBLICATIONS

Vahlquist, A. et al., "Isotretinoin Treatment of Severe Acne Affects the Endogenous Concentration of Vitamin A in Sebaceous Glands", *J. Invest. Dermatol.*, vol. 94, (1990), pp. 496–498.

Ellis, C. N. et al., "Treatment of actiically Aged Skin with Topical Tretinoin", *Pharmacology of Retinols in Skin*, vol. 3, (1989), pp. 249–252.

Lowe, N.J. et al., "Systemic Retinoids in Psoriasis: Comparative Efficacy and Toxicity", *Pharmacology of Retinols in Skin*, vol. 3, (1989), pp. 240–248.

Derwent Abstract of WO 94/03156 published Feb. 17, 1994.
Derwent Abstract of EP 0 388 275 published Sep. 19, 1990.
Derwent Abstract of EP 0 559 304 published Sep. 8, 1993.

*Primary Examiner*—Robert H. Harrison
*Attorney, Agent, or Firm*—Rimma Mitelman

[57] ABSTRACT

Fatty acid amides, but not free fatty acids or fatty acid esters, in combination with either retinol or retinyl ester resulted in a synergistic enhancement in keratinocyte proliferation and synergistic inhibition of keratinocyte differentiation. The effects of the retinol or retinyl esters in combination with fatty acid amides were analogous to treatment with retinoic acid.

9 Claims, No Drawings

SKIN CARE COMPOSITIONS CONTAINING FATTY ACID AMIDES AND RETINOL OR RETINYL ESTER

This is a continuation of Ser. No. 08/436,795, filed May 8, 1995, U.S. Pat. No. 5,599,548.

FIELD OF THE INVENTION

BACKGROUND OF THE INVENTION

Retinol (vitamin A) is an endogenous compound which occurs naturally in the human body and is essential for normal epithelial cell differentiation. Natural and synthetic vitamin A derivatives have been used extensively in the treatment of a variety of skin disorders and have been used as skin repair or renewal agents. Retinoic acid has been employed to treat a variety skin conditions, e.g., acne, wrinkles, psoriasis, age spots and discoloration. See e.g., Vahlquist, A. et al., *J. Invest. Dermatol.*, Vol. 94, Holland D. B. and Cunliffe, W. J. (1990), pp. 496–498; Ellis, C. N. et al., "Pharmacology of Retinols in Skin", Vasel, Karger, Vol. 3, (1989), pp. 249–252; Lowe, N. J. et al., "Pharmacology of Retinols in Skin", Vol. 3, (1989), pp. 240–248, PCT Patent Application No. WO 93/19743. Retinal and retinyl esters, such as retinyl acetate and retinyl palmitate, are easier to formulate/stabilize than retinoic acid. Unfortunately, retinol and retinyl esters are less effective than retinoic acid at providing skin benefits. The present invention is based, in part, on the discovery that certain combinations of retinol or retinyl esters with fatty acid amides result in a synergistic improvement in keratinocyte proliferation and differentiation. The effects of a fatty acid amide combined with retinol or a retinyl ester were analogous to the effects of retinoic acid. Thus, a mixture of fatty acid amides with retinol or retinyl esters mimics retinoic acid yet is easier to use than retinoic acid.

Thornfeldt (U.S. Pat. No. 5,057,501) discloses a method for treatment of papulosquamous and eczematous diseases with a composition containing a sesquiterpene compound and from about 0.025% to about 35% of a monocarboxylic fatty acid, ester, or amide. The compositions may also include a retinoid; Thornfeldt teaches that certain retinoids, namely isotretinoin, tretinoin, etretin (all of which are stereoforms of retinoic acid) and etretinate (an ester of trimethoxyphenyl retinoic acid) have proven efficacy against papulosquamous diseases. PCT Application WO/9325177 (Procter and Gamble) discloses compositions for topical application to skin which contain a specific type of acyclic carboxamide coolant and may include retinoids such as retinoic acid and its derivatives (e.g., cis and trans). PCT application WO/9403156 (Rhone Poulenc) discloses a topical composition containing linoleic acid or a derivative as an active ingredient for treatment and prophylaxis of impure skin (e.g., skin affected by pimples, pustules, or comedones); the composition may also contain 0.025–0.1 wt. % of tretinoin. European Patent Application No. 0 388 275 (Pierre Fabre Cosmetique) discloses compositions for treating seborrhea containing alkyl carboxamide and a zinc salt which may be zinc retinoate.

Klaus et al, (U.S. Pat. No. 5,216,148) disclose the use of specific complex carboxamides for treating and preventing neoplasms, dermatoses, and aging of skin. Van Scott et al. (U.S. Pat. No. 4,380,549) and Yu et al., (U.S. Pat. No. 4,363,815) disclose treatment of acne, dry, flaky, scaly skin with a hydroxyacid or the amide thereof. EP 582,458 discloses use of N,N-(1,4C alkyl) lauramide EP 559,304 disclose the use of an amide containing a hydrocarbyl chain of at least 25 carbon atoms as a skin smoothening agent. Beauquey et al. (U.S. Pat. No. 5,308,551) disclose a skin washing and conditioning composition containing, among other ingredients, a 1–4C alkanolamide of a 8–16C fatty acid. Great Britain Patent Specification No. 1,126,289 (Hoffman-La Roche) discloses a stock vitamin preparation containing vitamin A alcohol or a vitamin A ester, an emulsifier and a solvent which is selected from an alcohol or a dialkyl amide of a monocarboxylic acid (e.g., N,N-diethyl-acetamide, N,N-dimethyl acetamide or N,N-dimethyl formamide). The vitamin preparation has a very high vitamin content, i.e., the minimum concentration is 250,000 I.U. vitamin A/ml. Further, the amides disclosed in the '289 application do not fall within the scope of the present invention.

The art cited above does not disclose skin conditioning compositions based on synergistic combinations of a fatty acid amide with retinol or a retinyl ester. None of the art cited above addresses the need for an effective alternative to retinoic acid.

Accordingly, it is an object of the present invention to provide a skin conditioning composition containing a combination of retinol or a retinyl ester with certain fatty acid amides.

It is another object of the invention to provide a method of conditioning skin with a composition containing as an active system a mixture of certain fatty acid amides with retinol or a retinyl ester.

It is yet another object of the invention to provide a substitute for retinoic acid in cosmetic compositions.

These and other objects of the invention will become more apparent from the detailed description and examples that follow.

SUMMARY OF THE INVENTION

The above objects are attained by the present invention which includes, in part, a skin conditioning composition containing:

(a) from about 0.001% to about 10% of retinol or a retinyl ester;

(b) from about 0.0001% to about 50% of a fatty acid amide wherein the fatty acid contains at least 6 carbon atoms, and (c) a cosmetically acceptable vehicle.

The term "conditioning" as used herein means prevention and treatment of dry skin, photodamaged skin, appearance of wrinkles, age spots, aged skin, increasing stratum corneum flexibility, and generally increasing the quality of skin. The composition may be used to improve skin desquamation and epidermal differentiation.

The presence of the fatty acid amide in the inventive product substantially improves the performance of retinol or a retinyl ester, i.e., the activity enhancer substantially increases the ability of retinol or a retinyl ester to affect cellular proliferation and differentiation. The fatty acid amide has no or little effect on improving skin benefit when used alone; a substantial increase in skin benefit is only realized when the amide is combined with retinol or a retinyl ester. In short, the present invention is based, at least in part, on the discovery of synergistic interaction between retinol or a retinyl ester and certain fatty acid amides.

In a preferred embodiment of the invention, retinol or a retinyl ester is used in conjunction with an amide of $C_8$–$C_{24}$ fatty acid, most preferably a mono- or dialkanolamide of a $C_8$–$C_{24}$ fatty acid.

According to the present invention, by virtue of including an effective amount of a fatty acid amide into compositions containing retinol or a retinyl ester, the performance of the compositions is substantially improved. Alternatively, lower levels of retinol or a retinyl ester may be included in the composition containing the fatty acid amide to equal the performance of a similar formulation without the amide.

DESCRIPTION OF THE PREFERRED EMBODIMENT

The inventive compositions contain, as a first essential ingredient, a compound selected from the group consisting of retinol or a retinyl ester. The term "retinol" includes the following isomers of retinal: all-trans-retinol, 13-cis-retinol, 11-cis-retinol, 9-cis-retinol, 3,4-didehydro-retinol. Preferred isomers are all-trans-retinol, 13-cis-retinol, 3,4-didehydro-retinol, 9-cis-retinol. Most preferred is all-trans-retinol, due to its wide commercial availability.

Retinyl ester is an ester of retinol. The term "retinol" has been defined above. Retinyl esters suitable for use in the present invention are $C_1$–$C_{30}$ esters of retinol, preferably $C_2$–$C_{20}$ esters, and most preferably $C_2$, $C_3$, and $C_{16}$ esters because they are more commonly available. Examples of retinyl esters include but are not limited to: retinyl palmitate, retinyl formate, retinyl acetate, retinyl propionate, retinyl butyrate, retinyl valerate, retinyl isovalerate, retinyl hexanoate, retinyl heptanoate, retinyl octanoate, retinyl nonanoate, retinyl decanoate, retinyl undecandate, retinyl laurate, retinyl tridecanoate, retinyl myristate, retinyl pentadecanoate, retinyl heptadeconoate, retinyl stearate, retinyl isostearate, retinyl nonadecanoate, retinyl arachidonate, retinyl behenate, retinyl linoleate, retinyl oleate.

The preferred ester for use in the present invention is selected from retinyl palmitate, retinyl acetate and retinyl propionate, because these are the most commercially available and therefore the cheapest.

Retinol or retinyl ester is employed in the inventive composition in an amount of from about 0.001% to about 10%, preferably in an amount of from about 0.01% to about 1%, most preferably in an amount of from about 0.01% to about 0.5%.

The second essential ingredient of the inventive compositions is a fatty acid amide. It was found as part of the present invention that amides of short-chain carboxylic acids did not improve the performance of retinol or a retinyl ester. Thus, the present invention includes amides of fatty acids, wherein the fatty acid contains at least 6 carbon atoms. Suitable fatty acids include saturated and unsaturated, straight or branched fatty acids. Suitable fatty acids generally contain from 8 to 24 carbon atoms, preferably from 12 to 20 carbon atoms, and most preferably from 12 to 18 carbon atoms, because longer chain fatty acid amides are more beneficial for conditioning of the skin. In the most preferred embodiment of the invention, amides of essential fatty acids are employed because essential fatty acids provide nutrition for the skin. Examples of essential fatty acids include but are not limited to linoleic, linolenic, arachidonic, gamma-linolenic, homo-gamma-linolenic, and mixtures thereof. Linoleic acid is most preferred because it is also a precursor to ceramide.

Amides suitable for use in the present invention may be simple amides (i.e., those containing a —$CONH_2$ group), N-alkyl amides, N,N-dialkyl amides, mono-alkanol amides, and di-alkanol amides. Suitable alkyl or alkanol groups contain from 1 to 30 carbon atoms, preferably from 1 to 20 carbon atoms, and most preferably from 1 to 8 carbon atoms. The preferred amides included in the present invention are mono- and di-alkanol amides, particularly of essential fatty acids. Alkanol amides are more commonly available than alkyl amides.

The preferred fatty acid amides are selected from mono- and diethanolamides of linoleic acid, palmitic acid, and coconut oil.

The amide is included in the inventive compositions in an amount ranging from about 0.0001% to about 50%, preferably from about 0.01% to about 10%, most preferably from about 0.1% to about 5%.

The ratio of retinol to a fatty acid amide in the inventive compositions is generally in the range of from about 200:1 to about 1:50, preferably in the range of from about 100:1 to about 1:50, most preferably from about 50:1 to about 1:50.

The ratio of a retinyl ester to a fatty acid amide in the inventive compositions is generally in the range from about 3500:1 to about 1:300, preferably in the range of from about 300:1 to about 1:300, most preferably from about 50:1 to about 1:50.

Optional Skin Benefit Materials and Cosmetic Adjuncts

An oil or oily material may be present, together with an emulsifier to provide either a water-in-oil emulsion or an oil-in-water emulsion, depending largely on the average hydrophilic-lipophilic balance (HLB) of the emulsifier employed.

Various types of active ingredients may be present in cosmetic compositions of the present invention. Various types of active ingredients may be present in cosmetic compositions of the present invention. Actives are defined as skin or hair benefit agents other than emollients and other than ingredients that merely improve the physical characteristics of the composition. Although not limited to this category, general examples include sunscreens, tanning agents.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Another preferred optional ingredient is selected from essential fatty acids (EFAs), i.e., those fatty acids which are essential for the plasma membrane formation of all cells, in keratinocytes EFA deficiency makes cells hyperproliferative. Supplementation of EFA corrects this. EFAs also enhance lipid biosynthesis of epidermis and provide lipids for the barrier formation of the epidermis. The essential fatty acids are preferably chosen from linoleic acid, γ-linolenic acid, homo -γ-linolenic acid, columbinic acid, eicosa-(n-6, 9,13)-trienoic acid, arachidonic acid, γ-linolenic acid, timnodonic acid, hexaenoic acid and mixtures thereof.

Emollients are often incorporated into cosmetic compositions of the present invention. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, Fullers earth, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these materials may range anywhere from 0.001% up to 20% by weight of the composition.

Use of the Composition

The composition according to the invention is intended primarily as a product for topical application to human skin, especially as an agent for conditioning and smoothening the skin, and preventing or reducing the appearance of wrinkled or aged skin.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

Product Form and Packaging

The topical skin treatment composition of the invention can be formulated as a lotion having a viscosity of from 4,000 to 10,000 mPas, a fluid cream having a viscosity of from 10,000 to 20,000 mPas or a cream or a gel having a viscosity of from 20,000 to 100,000 mPas or above. The composition can be packaged in a suitable container to suit its viscosity and intended use by the consumer. For example, a lotion or fluid cream can be packaged in a bottle or a roll-ball applicator, or a capsule, or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a cosmetically acceptable composition as herein defined.

The following specific examples further illustrate the invention, but the invention is not limited thereto.

MATERIALS AND METHODS

Cell Culture

Human keratinocytes, isolated from neonatal foreskin by trypsin treatment were grown in Dulbecco Modification Eagle (DME) Hams F12 (1:1) medium/10% fetal calf serum in the presence of irradiated 3T3 mouse fibroblasts for establishing dividing keratinocyte colonies. Cells were grown under the above condition until their second passage and kept frozen for future use. Frozen second passage keratinocytes were thawed and plated into the above medium and grown for five days before they were switched to a serum-free MCDB 153-based medium keratinocyte growth medium (KGM) from Clonetics Corporation, San Diego, Calif. containing 0.15 mM Ca, or keratinocyte serum-free media (KSFM) from GIBCO containing 0.09 mM Ca). On day 7, when the cells were 80–90% confluent, they were trypsinized and plated in the serum-free medium for the various experiments.

Thymidine Assay $^3$H-Thymidine Incorporation and Keratinocyte Proliferation

The incorporation of $^3$H-thymidine by cultured keratinocytes was used as an assay of keratinocyte proliferation. Thymidine is one of four deoxynucleosides which are the monomeric units of DNA, the universal library of genetic information in the animal kingdom. Prior to cell division of a somatic cell such as a keratinocyte, the complete genome of the cell undergoing cell division is replicated. This involves large scale DNA synthesis by the cell and enables both daughter cells to receive identical copies of the genetic material. When $^3$H-thymidine is included in the culture media of keratinocytes which are synthesizing DNA in preparation for cell division then the labelled nucleoside is incorporated into the newly synthesized DNA. The extent of incorporation of $^3$H-thymidine into a population of cells is proportional to the rate of DNA synthesis by this population of cells and therefore an indication of their cellular proliferation.

Keratinocytes (that were cultured as described above) were plated in 24 well plates at a density of 40,000 cells per well in 1 ml media. After incubation for four days or until the cells were 60–70% confluent, the media was changed. Test compounds were added (in triplicate) to the wells 24 hours after the media change, and four hours later 1 $\mu$Ci$^3$H-Thymidine in 50 $\mu$l media was added per well. Cells were incubated for a further 24 hours. Media was removed from the cells, 10% ice cold trichloro acetic acid (TCA) added and plates were incubated on ice for 30 minutes. Cells were washed five times with 5% TCA and allowed to dissolve in 500 $\mu$l 0.1M NaOH for at least one hour (usually overnight). The preparations were neutralized with 0.1M HCl; 50 $\mu$l of the cell preparation was used to determine total protein content. Disintegrations per minute (DPM) from $^3$H labelling of DNA was determined by liquid scintillation counting of 900 $\mu$l of the cell preparation. Thymidine incorporation results were expressed as DPM/$\mu$g protein.

Transglutaminase Assay
Transglutaminase Assay and Keratinocyte Differentiation During the process of terminal differentiation in the epidermis, a 15 nm thick layer of protein, known as the cornified envelope (CE) is formed on the inner surface of the cell periphery. The CE is composed of numerous distinct proteins which have been cross-linked together by the formation of $N^{\epsilon}$-($\gamma$-glutamyl)lysine isodipeptide bonds catalyzed by the action of at least two different transglutaminases (TGases) expressed in the epidermis. TGase I is expressed in abundance in the differentiated layers of the epidermis, especially the granular layer, but is absent in the undifferentiated basal epidermis. Thus TGase I is a useful marker of epidermal keratinocyte differentiation with high TGase I levels indicating a more differentiated state. An ELISA based TGase I assay, using a TGase I antibody, was used to assess the state of differentiation of the cultured keratinocytes in the examples that follow.

Keratinocytes (cultured as described above) were plated in 96 well plates at a density of 3,000 cells per well in 200 $\mu$l media. After incubation for four days the media was changed to media containing test compounds (six replicates per test). The cells were cultured for a further 72 hours after which time the media was aspirated and the plates stored at −70° C. Plates were removed from the freezer, and the cells washed with PBS. 100 $\mu$l sterile water was added and the cells were freeze fractured by freezing at −70° C. then thawing. The cells were incubated for one hour at room temperature (R/T) with PBS/3% BSA (wash buffer, bovine serum albumin), then rinsed with a fresh aliquot of wash buffer. Cells were incubated with 50 $\mu$l of primary antibodies monoclonal anti-human transglutaminase (IgG) obtained from Amersham (mouse) diluted 1:300 in wash buffer for one hour, 37° C. then rinsed two times with wash buffer. Cells were then incubated with 50 $\mu$l of secondary antibody (Feb fragment, peroxidase conjugated anti-mouse IgG obtaining from Amersham) diluted 1:200 in wash buffer for one hour at 37° C., then rinsed two times with wash buffer. Cells were incubated with substrate solution (4 mg o-phenylene diamine and 3.3 $\mu$l 30% $H_2O_2$ in 10 ml 0.1M citrate buffer pH 5.0) for five minutes, R/T, in darkness (under aluminum foil). The reaction was stopped by the addition of 50 $\mu$l 4N $H_2SO_4$. The absorbance of samples was read at 492 nm in the plate reader. Out of the six replicates, four were treated with both antibodies, two were treated only with the secondary antibody (i.e., to determine background binding of enzyme conjugated Ab). TGase levels were determined by subtracting background from the readings from each treatment and determining mean ±s.d. for the replicates exposed to both Ab.

EXAMPLE 1

Retinoic acid is more effective than retinol at altering keratinocyte differentiation state A. The effect on incorporation of $^3$H-thymidine $\mu$g soluble protein 24 hours after the addition of retinoic acid or retinol at various concentrations was examined. The results that were obtained are summarized in Table 1A.

TABLE 1A

Effect of Retinoic Acid (RA) and Retinol (ROH) on Keratinocyte Thymidine Incorporation

| Treatment | mean Thymidine incorp./$\mu$g protein ± s.d (% control) | p value vs Control | p value vs $10^{-7}$M ROH | p value vs $10^{-8}$M ROH | p value vs $10^{-9}$M ROH |
|---|---|---|---|---|---|
| Control | 2094 ± 140 (100%) | — | 0.202 | 0.501 | 0.203 |
| 2.5 × $10^{-7}$M RA | 2475 ± 116 (118%) | 0.005 | 0.032 | 0.004 | 0.002 |
| 2.5 × $10^{-7}$M ROH | 2218 ± 73 (106%) | 0.202 | — | 0.021 | 0.005 |
| 2.5 × $10^{-8}$M RA | 2686 ± 72 (128%) | 0.001 | 0.001 | 0.001 | 0.001 |
| 2.5 × $10^{-8}$M ROH | 2034 ± 46 (97%) | 0.501 | 0.021 | — | 0.121 |
| 2.5 × $10^{-9}$M RA | 2556 ± 80 (122%) | 0.001 | 0.006 | 0.001 | 0.001 |
| 2.5 × $10^{-9}$M ROH | 1977 ± 19 (94%) | 0.203 | 0.005 | 0.121 | — | n = 3

All concentrations of retinoic acid tested, i.e., 2.5×$10^{-7}$M, 2.5×$10^{-8}$ and 2.5×$10^{-9}$M, significantly increased keratinocyte proliferation over both the ethanol control and each of the 2.5×$10^{-7}$M, 2.5×$10^{-8}$M and 2.5×$10^{-9}$M retinol treatments and they did so in a dose dependant manner. This is consistent with retinoic acid having a greater stimulator effect on epithelial proliferation than retinol.

B. The effect on Transglutaminase levels after addition of retinoic acid and retinol was examined. The results that were obtained are summarized in Table 1B.

TABLE 1B

Effect of Retinoic Acid (RA) and Retinol (ROH) on Keratinocyte Transglutaminase Level

| Treatment | mean Transglutaminase ELISA level ± s.d (% control) | p value vs Control | p value vs $10^{-7}$M ROH | p value vs $10^{-8}$M ROH | p value vs $10^{-9}$M ROH |
|---|---|---|---|---|---|
| Control | 0.430 ± 0.069 (100%) | — | 0.001 | 0.632 | 0.121 |
| 2.5 × $10^{-7}$M RA | 0.088 ± 0.015 (20%) | 0.001 | 0.001 | 0.001 | 0.001 |

TABLE 1B-continued

Effect of Retinoic Acid (RA) and
Retinol (ROH) on Keratinocyte Transglutaminase Level

| Treatment | mean Transglutaminase ELISA level ± s.d (% control) | p value vs Control | p value vs $10^{-7}$M ROH | p value vs $10^{-8}$M ROH | p value vs $10^{-9}$M ROH |
|---|---|---|---|---|---|
| $2.5 \times 10^{-7}$M ROH | 0.290 ± 0.043 (67%) | 0.001 | — | 0.001 | 0.001 |
| $2.5 \times 10^{-8}$M RA | 0.268 ± 0.068 (62%) | 0.001 | 0.384 | 0.001 | 0.001 |
| $2.5 \times 10^{-8}$M ROH | 0.371 ± 0.054 (86%) | 0.632 | 0.001 | — | 0.024 |
| $2.5 \times 10^{-9}$M RA | 0.360 ± 0.067 (84%) | 0.360 | 0.006 | 0.650 | 0.018 |
| $2.5 \times 10^{-9}$M ROH | 0.416 ± 0.035 (97%) | 0.121 | 0.001 | 0.024 | — | n = 3

All concentrations of retinoic acid tested, i.e., $2.5 \times 10^{-7}$M, $2.5 \times 10^{-8}$M and $2.5 \times 10^{-9}$M decreased keratinocyte differentiation over both the ethanol control and did so to a significantly greater extent than each of the corresponding $2.5 \times 10^{-7}$M, $2.5 \times 10^{-8}$M and $2.5 \times 10^{-9}$M retinol treatments. The decrease in transglutaminase level was dose dependent for both retinoic acid and retinol. This is consistent with retinoic acid having a greater inhibitory effect on epithelial differentiation than retinol.

EXAMPLE 2

Linoleoyl-diethanolamide (Linoleoyl-DEA) and retinol act synergistically to enhance keratinocyte proliferation and to inhibit differentiation A. The effect on incorporation of $^3$H-thymidine/µg soluble protein 24 hours after addition of the test compounds was examined and the combined results of three independent experiments were normalized to their respective ethanol controls. The results that were obtained are summarized in Table 2A.

$2.5 \times 10^{-8}$M retinoic acid significantly increased keratinocyte thymidine incorporation over both the ethanol control (by 26%) and the $2.5 \times 10^{-8}$M retinol treatment (by 24%). Each of $2.5 \times 10^{-8}$M ROH and $10^{-9}$M linoleoyl-DEA had a minor, non-significant stimulatory effect on keratinocyte proliferation. However, the combination of $2.5 \times 10^{-8}$M retinol+$10^{-9}$M linoleoyl-DEA significantly increased keratinocyte proliferation over both the ethanol (by 22%) and the $2.5 \times 10^{-8}$M retinol (by 17%) treatments. Linoleoyl-DEA and retinol therefore, act synergistically to increase keratinocyte proliferation to levels which closely resemble the stimulatory effect of retinoic acid.

B. The effect on transglutaminase 1 (TG1) levels was examined in response to a 72 hour treatment with the test compounds and the combined results of three independent experiments were normalized to their respective ethanol controls. The results that were obtained are summarized in Table 2B.

TABLE 2A

Effect of Retinol and Linoleoyl-DEA on Keratinocyte Thymidine Incorporation

| Treatment | mean Thymidine incorp./µg protein ± s.d (% control) | p value vs Control | p value vs $10^{-8}$M ROH | p value vs $10^{-9}$M lino'-DEA |
|---|---|---|---|---|
| Control | 1.000 ± 0.117 (100%) | — | 0.001 | 0.632 |
| $2.5 \times 10^{-8}$M RA | 1.255 ± 0.139 (126%) | 0.007 | 0.002 | 0.011 |
| $2.5 \times 10^{-8}$M ROH | 1.025 ± 0.152 (102%) | 0.870 | — | 0.557 |
| $10^{-9}$M linoleoyl-DEA | 1.052 ± 0.158 (105%) | 0.308 | 0.557 | — |
| $2.5 \times 10^{-8}$M ROH + $10^{-9}$M linoleoyl-DEA | 1.216 ± 0.131 (122%) | 0.001 | 0.007 | 0.030 |

TABLE 2B

Effect of Retinol and Linoleoyl-DEA on keratinocyte TGase

| Treatment | mean TGase ± s.d (% control) | p value vs Control | p value vs $10^{-8}$M ROH | p value vs $10^{-9}$M lino'-DEA |
|---|---|---|---|---|
| Control | 1.000 ± 0.518 (100%) | — | 0.001 | 0.001 |
| $2.5 \times 10^{-7}$M RA | 0.283 ± 0.470 (28%) | 0.001 | 0.002 | 0.019 |
| $2.5 \times 10^{-7}$M ROH | 0.594 ± 0.542 (59%) | 0.001 | — | 0.996 |

TABLE 2B-continued

Effect of Retinol and Linoleoyl-DEA on keratinocyte TGase

| Treatment | mean TGase ± s.d (% control) | p value vs Control | p value vs $10^{-8}$M ROH | p value vs $10^{-9}$M lino'-DEA |
|---|---|---|---|---|
| $10^{-6}$M linoleoyl-DEA | 0.594 ± 0.773 (59%) | 0.001 | 0.996 | — |
| 2.5 × $10^{-7}$M RCH + $10^{-6}$M linoleoyl-DEA | −0.086 ± 0.551 (0%) | 0.001 | 0.001 | 0.001 | n = 9

$2.5 \times 10^{-7}$M retinoic acid was very effective at repressing keratinocyte TG1 levels (to 28% of control level). $2.5 \times 10^{-7}$ retinol also repressed TG1 levels (to 59% of control) but not as effectively as retinoic acid, $10^{-6}$M linoleoyl-DEA on its own also repressed keratinocyte TG1 levels. However, the combination of $2.5 \times 10^{-7}$M retinol+$10^{-6}$M linoleoyl-DEA repressed keratinocyte TG1 completely to undetectable levels. Linoleoyl-DEA and retinol therefore, act synergistically to repress keratinocyte differentiation in a manner analogous to the effect of retinoic acid.

EXAMPLE 3

Linoleoyl-DEA and Retinyl Palmitate Synergistically Enhanced Keratinocyte Proliferation and Inhibited Differentiation A. The effect of linoleoyl-DEA and the retinyl ester (retinyl palmitate) on incorporation of $^3$H-thymidine was examined. The results that were obtained are summarized in Table 3A.

The retinoic acid positive control significantly increased keratinocyte thymidine incorporation over both the ethanol control (by 17%) and the $2.5 \times 10^{-7}$M retinyl palmitate treatment (by 6%). $10^{-8}$M linoleoyl-DEA had no effect on keratinocyte proliferation. $2.5 \times 10^{-7}$M retinyl palmitate increased keratinocyte thymidine incorporation over the control in this experiment. However, the combination of $2.5 \times 10^{-7}$M retinyl palmitate+$10^{-8}$M linoleoyl-DEA significantly increased keratinocyte proliferation over both the ethanol (by 18%) and the $2.5 \times 10^{-7}$M retinyl palmitate (by 7%) treatments. Linoleoyl-DEA and retinyl palmitate therefore, act synergistically to increase keratinocyte proliferation to levels which closely resemble the stimulatory effect of retinoic acid.

B. The effect on TG1 in response to treatment with retinyl palmitate and linoleoyl-DEA was examined. The results that were obtained are summarized in Table 3B.

TABLE 3A

Effect of Retinyl Palmitate (RP) and Linoleoyl-DEA on Keratinocyte Thymidine Incorporation

| Treatment | mean Thymidine incorp./μg protein ± s.d (control %) | p value vs Control | p value vs $10^{-7}$M RP | p value vs $10^{-8}$M lino'-DEA |
|---|---|---|---|---|
| Control | 1702 ± 99 (100%) | — | 0.025 | 0.873 |
| 2.5 × $10^{-9}$M RA | 1090 ± 61 (117%) | 0.003 | 0.106 | 0.003 |
| 2.5 × $10^{-7}$M Retinyl palmitate (RP) | 1884 ± 64 (111%) | 0.025 | — | 0.014 |
| $10^{-8}$M linoleoyl-DEA | 1692 ± 48 (99%) | 0.873 | 0.014 | — |
| 2.5 × $10^{-7}$M RP + $10^{-8}$M linoleoyl-DEA | 2007 ± 43 (118%) | 0.002 | 0.050 | 0.001 | n = 3

TABLE 3B

Effect of Retinyl Palmitate (RP) and Linoleoyl-DEA on Keratinocyte TGase Levels

| Treatment | mean TGase ± s.d (% control) | p value vs Control | p value vs $10^{-8}$M RP | p value vs $10^{-6}$M lino'-DEA |
|---|---|---|---|---|
| Control | 0.218 ± 0.087 (100%) | — | 0.130 | 0.268 |
| 2.5 × $10^{-7}$M RA | 0.073 ± 0.022 (33%) | 0.001 | 0.001 | 0.001 |
| 2.5 × $10^{-7}$M Retinyl palmitate (RP) | 0.177 ± 0.026 (82%) | 0.130 | — | 0.636 |
| $10^{-6}$M linoleoyl-DEA | 0.186 ± 0.058 (85%) | 0.268 | 0.636 | — |
| 2.5 × $10^{-7}$M RP + $10^{-6}$M linoleoyl-DEA | 0.046 ± 0.013 (21%) | 0.001 | 0.001 | 0.001 | n = 3

$2.5\times10^{-7}$M retinoic acid was the most effective treatment at repressing keratinocyte TG1 levels (to 33% of control level). $2.5\times10^{-7}$M retinyl palmitate also repressed TG1 levels to 82% of control levels but not as effective as retinoic acid. $10^{-6}$M linoleoyl-DEA on its own had very little effect on keratinocyte TG1 levels. However, the combination of $2.5\times10^{-7}$M retinyl palmitate+$10^{-6}$M linoleoyl-DEA repressed keratinocyte TG1 levels to 21% of control level. Linoleoyl-DEA and retinyl palmitate therefore, act synergistically to repress keratinocyte differentiation in a manner analogous to the effect of retinoic acid.

EXAMPLE 4

Cocoyl-DEA, Cocoyl-MEA, Palmitoyl-MEA and Linoleoyl-MEA Each Act in Synergy With Retinol A. The effect on TG1 in response to treatment with retinol and cocoyl-diethanolamide (cocoyl-DEA), another example of a fatty acid amide, was examined. The results that were obtained are summarized in Table 4A.

TABLE 4A

Effect of Retinol and Cocoyl-DEA on Keratinocyte TGase Levels

| Treatment | mean TGase ± s.d (% control) | p value vs Control | p value vs $10^{-7}$M ROH | p value vs $10^{-7}$M coco'-DEA |
|---|---|---|---|---|
| Control | 0.177 ± 0.180 (100%) | — | 0.001 | 0.113 |
| $2.5\times10^{-7}$M RA | 0.058 ± 0.698 (33%) | 0.001 | 0.466 | 0.197 |
| $2.5\times10^{-7}$M Retinol | 0.145 ± 0.070 (82%) | 0.001 | — | 0.410 |
| $10^{-7}$M Cocoyl-DEA | 0.187 ± 0.111 (106%) | 0.268 | 0.636 | — |
| $2.5\times10^{-7}$M Retinol + $10^{-7}$M Cocoyl-DEA | 0.031 ± 0.114 (17%) | 0.001 | 0.001 | 0.001 | n = 3

$2.5\times10^{-7}$M retinoic acid repressed keratinocyte TG1 levels to 33% of control level. $2.5\times10^{-7}$ retinol also repressed TG1 levels, to 82% of control levels—not as effectively as retinoic acid. $10^{-7}$M cocoyl-DEA on its own had no effect on TG1 levels. The combination of $2.5\times10^{-7}$M ROH+$10^{7}$M cocoyl-DEA repressed TG1 level to 17% of control level. Therefore, this combination had a greater effect on keratinocyte TG1 levels than the combined effect of retinol or cocoyl-DEA alone. Retinol and cocoyl-DEA act synergistically on keratinocytes to enhance TG1 levels.

B. The effect on TG1 in response to treatment with retinol and cocoyl-monoethanoamide (cocoyl-MEA), another example of a fatty acid amide was examined. The results that were obtained are summaried in Table 4B.

TABLE 4B

Effect of Retinol and Cocoyl-MEA on Keratinocyte TGase Levels

| Treatment | mean TGase ± s.d (% control) | p value vs Control | p value vs $10^{-7}$M ROH | p value vs $10^{-8}$M coco'-MEA |
|---|---|---|---|---|
| Control | 0.123 ± 0.051 (100%) | — | 0.001 | 0.001 |
| $2.5\times10^{-8}$M RA | 0.036 ± 0.009 (29%) | 0.001 | 0.001 | 0.001 |
| $2.5\times10^{-8}$M Retinol | 0.054 ± 0.013 (44%) | 0.001 | — | 0.001 |
| $10^{-8}$M Cocoyl-MEA | 0.115 ± 0.017 (93%) | 0.086 | 0.001 | — |
| $2.5\times10^{-8}$M Retinol + $10^{-8}$M Cocoyl-MEA | 0.041 ± 0.011 (33%) | 0.001 | 0.018 | 0.001 | n = 3

$2.5\times10^{-8}$M retinoic acid repressed keratinocyte TG1 levels to 29% of control level. $2.5\times10^{-8}$ retinol also repressed TG1 levels to 44% of control levels but not as effectively as retinoic acid. $10^{-8}$M cocoyl-MEA on its own had virtually no effect on TG1 levels. The combination of $2.5\times10^{-8}$M ROH+$10^{-8}$M cocoyl-MEA repressed TG1 levels to 33% of control levels therefore the combination had a greater effect on keratinocyte TG1 levels than either of the treatments alone. Retinol and cocoyl-MEA act synergistically to repress keratinocyte TG1 levels.

C. The effect of retinol and palmitoyl-monoethanolamide (palmitoyl-MEA), another fatty acid amide, on incorporation by keratinocytes of $^3$H-thymidine was examined. The results that were obtained are summarized in Table 4C.

TABLE 4C

Effect of Retinol and Palmitoyl-MEA on
Keratinocyte Thymidine Incorporation

| Treatment | mean Thymidine incorp./μg protein ± s.d (% control) | p value vs Control | p value vs $10^{-7}$M ROH | p value vs $10^{-6}$M palm'-MEA |
|---|---|---|---|---|
| Control | 1.000 ± 0.102 (100%) | — | 0.813 | 0.591 |
| 2.5 × $10^{-8}$M RA | 1.164 ± 0.113 (116%) | 0.016 | 0.043 | 0.0018 |
| 2.5 × $10^{-8}$M Retinol | 1.012 ± 0.088 (101%) | 0.813 | — | 0.360 |
| $10^{-6}$M palmitoyl-MEA | 0.974 ± 0.080 (97%) | 0.591 | 0.360 | — |
| 2.5 × $10^{-8}$M Retinol + $10^{-6}$M palmitoyl-MEA | 1.108 ± 0.083 (111%) | 0.044 | 0.038 | 0.007 | n = 3

2.5×$10^{-8}$M retinoic acid significantly increased keratinocyte thymidine incorporation over both the ethanol control by 16% and the 2.5×$10^{-8}$M retinol treatment by 15%. Neither $10^{-8}$M palmitoyl-MEA nor 2.5×$10^{-8}$M retinol had an effect on keratinocyte proliferation compared to the control. However, the combination of 2.5×$10^{-8}$M retinol + $10^{-6}$M palmitoyl-MEA significantly increased keratinocyte proliferation over both the ethanol control (by 11%) and the 2.5×$10^{-8}$M retinol treatment (by 10%). Palmitoyl-MEA and retinol therefore, act synergistically to increase keratinocyte proliferation to levels which closely resemble the stimulatory effect of retinoic acid.

D. The effect on incorporation of $^3$H-thymidine/μg soluble protein 24 hours after addition of linoleoyl-monoethanolamide (linoleyol-MEA) was examined and the results were normalized to the ethanol control. The results that were obtained are summarized in Table 4D.

$10^{-9}$M linoleoyl-MEA had an inhibitory effect on keratinocyte proliferation. However the combination of 2.5×$10^{-8}$M retinol+$10^{-9}$M linoleoyl-MEA significantly increased keratinocyte proliferation over both the ethanol (by 39%) and the 2.5×$10^{-8}$M retinol (by 33%) treatments. Linoleoyl-MEA and retinol therefore, act synergistically to increase keratinocyte proliferation to levels which closely resemble the stimulatory effect of retinoic acid.

EXAMPLE 5

Linoleic Acid and The Methyl Ester of Linoleic Acid Show No Synergy With Retinol A. The effect on TG1 in response to treatment with retinol and linoleic acid, was examined. The results that were obtained are summarized in Table 5A.

TABLE 4D

Effect of Retinol and Linoleoyl-MEA on
Keratinocyte Thymidine Incorporation

| Treatment | mean Thymidine incorp./μg protein ± s.d (% control) | p value vs Control | p value vs $10^{-8}$M ROH | p value vs $10^{-9}$ lino'-MEA |
|---|---|---|---|---|
| Control | 1.00 ± 0.34 (100%) | — | 0.710 | 0.063 |
| 2.5 × $10^{-8}$M RA | 1.47 ± 0.36 (147%) | 0.015 | 0.003 | 0.001 |
| 2.5 × $10^{-8}$M ROH | 1.06 ± 0.27 (106%) | 0.710 | — | 0.004 |
| $10^{-9}$M linoleoyl-MEA | 0.67 ± 0.18 (67%) | 0.063 | 0.004 | — |
| 2.5 × $10^{-8}$M ROH + $10^{-9}$M linoleoyl-MEA | 1.39 ± 0.34 (139%) | 0.032 | 0.007 | 0.001 | n = 3

2.5×$10^{-8}$M retinoic acid significantly increased keratinocyte thymidine incorporation over both the ethanol control (by 47%) and the 2.5×$10^{-8}$M retinal treatment (by 41%).

TABLE 5A

Effect of Retinol and Linoleic Acid on Keratinocyte TGase Levels

| Treatment | mean TGase ± s.d (% control) | p value vs Control | p value vs $10^{-7}$M ROH | p value vs $10^{-6}$M LA |
|---|---|---|---|---|
| Control | 0.108 ± 0.085 (100%) | — | 0.075 | 0.103 |
| 2.5 × $10^{-7}$M RA | −0.004 ± 0.103 (0%) | 0.003 | 0.409 | 0.002 |
| 2.5 × $10^{-7}$M Retinol | 0.042 ± 0.112 (39%) | 0.001 | — | 0.020 |
| $10^{-6}$M Linoleic acid (LA) | 0.161 ± 0.061 (>100%) | 0.103 | 0.020 | — |
| 2.5 × $10^{-7}$M ROH + $10^{-6}$M Linoleic acid | 73 ± 0.071 (68%) | 0.001 | 0.476 | 0.001 | n = 3

$2.5 \times 10^{-7}$M retinoic acid repressed keratinocyte TG1 levels completely in this experiment. $2.5 \times 10^{-7}$M retinol also repressed TG1 levels to 39% of control levels but not as effectively as retinoic acid. $10^{-6}$M linoleic acid appeared to stimulate TG1. The combination of $2.5 \times 10^{-8}$M ROH+$10^{-8}$M linoleic acid reduced the effectiveness (i.e., with respect to TGI inhibition) of the retinol treatment. No synergy was therefore observed between retinol and linoleic acid.

B. The effect on TG1 in response to treatment with retinol and methyl linoleate, an example of a linoleic acid ester was examined. The results that were obtained are summarized in Table 5B.

$2.5 \times 10^{-7}$M retinoic acid was very effective at repressing keratinocyte TG1 levels (to 28% of control level). $2.5 \times 10^{-7}$M retinol also repressed TG1 levels (to 71% of control) but not as effectively as retinoic acid. $10^{-7}$M formamide had a small inhibitory effect on keratinocyte TG1 levels. $2.5 \times 10^{-7}$M retinol+$10^{-7}$M palmitoyl-DEA had no effect on keratinocyte TG1 levels compared to the control treatment and in fact was significantly less effective than $2.5 \times 10^{-7}$M retinol alone. Formamide and retinol therefore, do not act synergistically to repress keratinocyte differentiation.

B. The effect on transglutaminase 1 (TG1) levels was examined in response to a 72 hour treatment with retinol and acetamide ($C^2$ fatty acid amide) and the results are shown in Table 6B.

TABLE 5B

Effect of Retinol and Methyl Linoleate on Keratinocyte TGase Levels

| Treatment | mean TGase ± s.d (% control) | p value vs Control | p value $10^{-8}$M ROH | p value vs $10^{-8}$M Methyl Linoleate |
|---|---|---|---|---|
| Control | 0.289 ± 0.128 (100%) | — | 0.039 | 0.016 |
| $2.5 \times 10^{-8}$M RA | 0.092 ± 0.030 (32%) | 0.001 | 0.001 | 0.001 |
| $2.5 \times 10^{-8}$M Retinol | 0.199 ± 0.093 (69%) | 0.039 | — | 0.837 |
| $10^{-8}$M Methyl linoeale | 0.193 ± 0.033 (67%) | 0.016 | 0.837 | — |
| $2.5 \times 10^{-8}$M ROH + $10^{-8}$M Methyl linoleate | 0.210 ± 0.031 (73%) | 0.045 | 0.703 | 0.209 | n = 3

$2.5 \times 10^{-8}$M retinoic acid repressed keratinocyte TG1 levels (to 32% of control level). $2.5 \times 10^{-8}$M retinol also repressed TG1 levels to 69% of control levels but not as effectively as retinoic acid. $10^{-8}$M methyl linoleate on its own repressed TG1 to the same extent as $2.5 \times 10^{-8}$M retinol but not as well as $2.5 \times 10^{-8}$M retinoic acid. The combination of $2.5 \times 10^{-8}$M ROH+$10^{-8}$M Methyl linoleate had no further effect on keratinocyte TG1 levels than either of the retinol or methyl linoleate treatments alone. No synergy was therefore observed between retinol and the methyl ester of linoleic acid.

EXAMPLE 6

Short Chain Fatty Acid Amides (i.e.. $C_1$, $C_2$ and $C_5$, Showed No Synergy With Retinol A. The effect on transglutaminase 1 (TG1) levels was examined in response to a 72 hour treatment with retinol and formamide ($C_1$ fatty acid amide) and the results are shown in Table 6A.

TABLE 6A

Effect of Retinol and Formamide on Keratinocyte TGase

| Treatment | mean Thymidine incorp./μg protein ± s.d (% control) | p value vs Control | p value vs $10^{-7}$M ROH | p value vs $10^{-7}$M C1 |
|---|---|---|---|---|
| Control | 0.488 ± 0.134 (100%) | — | 0.002 | 0.079 |
| $2.5 \times 10^{-7}$M RA | 0.137 ± 0.024 (28%) | 0.001 | 0.001 | 0.001 |
| $2.5 \times 10^{-7}$M ROH | 0.351 ± 0.046 (71%) | 0.002 | — | 0.016 |
| $10^{-7}$M Formamide (Cl) | 0.413 ± 0.069 (85%) | 0.079 | 0.016 | — |
| $2.5 \times 10^{-7}$M ROH + $10^{-7}$M Formamide | 0.514 ± 0.074 (105%) | 0.541 | 0.001 | 0.002 | n = 3

TABLE 6B

Effect of Retinol and Acetamide on Keratinocyte TGase

| Treatment | mean Thymidine incorp./μg protein ± s.d (% control) | p value vs Control | p value vs $10^{-7}$M ROH | p value vs $10^{-7}$M C2 |
|---|---|---|---|---|
| Control | 0.491 ± 0.077 (100%) | — | 0.001 | 0.662 |
| 2.5 × $10^{-7}$M RA | 0.226 ± 0.069 (46%) | 0.001 | 0.001 | 0.001 |
| 2.5 × $10^{-7}$M ROH | 0.317 ± 0.043 (65%) | 0.001 | — | 0.001 |
| $10^{-7}$M Acetamide (C2) | 0.480 ± 0.042 (98%) | 0.662 | 0.001 | — |
| 2.5 × $10^{-7}$M ROH + $10^{-7}$M Acetamide | 0.503 ± 0.054 (102%) | 0.622 | 0.001 | 0.260 | n = 3

$2.5 \times 10^{-7}$M retinoic acid was effective at repressing keratinocyte TG1 levels (to 46% of control level). $2.5 \times 10^{-7}$M retinol also repressed TG1 levels (to 65% of control) but not as effectively as retinoic acid. $10^{-7}$M acetamide had no effect on keratinocyte TG1 levels. $2.5 \times 10^{-7}$M retinol+$10^{-7}$M palmitoyl-DEA also had no effect on keratinocyte TG1 levels compared to the control treatment and in fact was significantly less effective than $2.5 \times 10^{-7}$M retinol alone. Acetamide and retinol therefore, do not act synergistically to repress keratinocyte differentiation.

C. The effect on transglutaminase 1 (TG1) levels was examined in response to a 72 hour treatment with palmitoyl-DEA ($C_5$ fatty acid amide) and retinol and the results are shown in Table 6C.

keratinocyte TG1 to levels which were similar to those of $2.5 \times 10^{-7}$M retinol alone. Palmitoyl-DEA and retinol therefore, do not act synergistically to repress keratinocyte differentiation.

EXAMPLE 7

The Synergistic Increase in Keratinocyte Proliferation Induced By Retinol and Fatty Acid Amide is Most Effective at ROH: Fatty Acid Amide Ratios Ranging From 200:1 to 1:50

In order to determine the range of retinol:linoleoyl-DEA ratios which were most effective at enhancing the benefit of retinol the effect on incorporation of $^3$H-thymidine/μg

TABLE 6C

Effect of Retinol and Pentanoyl-DEA on Keratinocyte TGase

| Treatment | mean Thymidine incorp./μg protein ± s.d (% control) | p value vs Control | p value vs $10^{-7}$M ROH | p value vs $10^{-7}$M C5-DEA |
|---|---|---|---|---|
| Control | 0.430 ± 0.069 (100%) | — | 0.001 | 0.099 |
| 2.5 × $10^{-7}$M RA | 0.088 ± 0.015 (20%) | 0.001 | 0.001 | 0.001 |
| 2.5 × $10^{-7}$M ROH | 0.290 ± 0.043 (67%) | 0.001 | — | 0.001 |
| $10^{-7}$M Pentonoyl-DEA (C5-DEA) | 0.425 ± 0.079 (99%) | 0.099 | 0.001 | — |
| 2.5 × $10^{-7}$M ROH + $10^{-7}$M Pentanoyl-DEA | 0.291 ± 0.093 (68%) | 0.002 | 0.978 | 0.001 | n = 3

$2.5 \times 10^{-7}$M retinoic acid was very effective at repressing keratinocyte TG1 levels (to 20% of control level). $2.5 \times 10^{-7}$M retinol also repressed TG1 levels (to 67% of control) but not as effectively as retinoic acid. $10^{-7}$M pentanoyl-DEA on its own had no effect on keratinocyte TG1 levels. Moreover $2.5 \times 10^{-7}$M retinol+$10^{-7}$M polmitoyl-DEA only repressed soluble protein 24 hours after the addition of retinol and linoleoyl-DEA in different ratios of amounts, was examined. These were compared to the effects of retinoic acid at equimolar concentrations (with respect to retinol) and the effects of retinol and linoleoyl-DEA alone. The results that were obtained are presented in Table 7A.

TABLE 7A

| Treatment | mean Thymidine incorp/μg protein ± s.d (% control) | p value vs Control | p value vs $10^{-n}$M ROH | p value vs $10^{-n}$M RA | p value vs $10^{-n}$M lino'-DEA |
|---|---|---|---|---|---|
| Control | 1.000 ± 0.117 (100%) | — | — | — | — |
| 2.5 × $10^{-7}$M RA | 1.129 ± 0.109 (113%) | 0.007 | 0.133 | — | — |
| 2.5 × $10^{-8}$M RA | 1.255 ± 0.139 (126%) | 0.001 | 0.002 | — | — |
| 2.5 × $10^{-9}$M RA | 1.208 ± 0.128 (121%) | 0.001 | 0.002 | — | — |
| 2.5 × $10^{-7}$M Retinol | 1.025 ± 0.165 (102%) | 0.633 | — | 0.133 | — |
| 2.5 × $10^{-8}$M Retinol | 1.008 ± 0.152 (101%) | 0.870 | — | 0.002 | — |
| 2.5 × $10^{-9}$M Retinol | 0.995 ± 0.123 (100%) | 0.919 | — | 0.002 | — |
| $10^{-6}$M linoleoyl-DEA | 0.607 ± 0.080 (61%) | 0.001 | — | — | — |
| $10^{-7}$M linoleoyl-DEA | 1.010 ± 0.075 (101%) | 0.821 | — | — | — |
| $10^{-8}$M linoleoyl-DEA | 1.137 ± 0.206 (114%) | 0.796 | — | — | — |

TABLE 7A-continued

| Treatment | mean Thymidine incorp/μg protein ± s.d (% control) | p value vs Control | p value vs $10^{-n}$M ROH | p value vs $10^{-n}$M RA | p value vs $10^{-n}$M lino'-DEA |
|---|---|---|---|---|---|
| $10^{-9}$M linoleoyl-DEA | 1.052 ± 0.158 (105%) | 0.308 | — | — | — |
| 2.5 × $10^{-7}$M ROH + $10^{-6}$M linoleoyl-DEA | 1.214 ± 0.095 (121%) | 0.001 | 0.025 | 0.142 | 0.001 |
| 2.5 × $10^{-7}$M ROH + $10^{-7}$M linoleoyl-DEA | 1.225 ± 0.080 (122%) | 0.001 | 0.005 | 0.049 | 0.001 |
| 2.5 × $10^{-7}$M ROH + $10^{-9}$M linoleoyl-DEA | 1.186 ± 0.072 (119%) | 0.001 | 0.016 | 0.204 | 0.035 |
| 2.5 × $10^{-7}$M ROH + $10^{-10}$M linoleoyl-DEA | 0.930 ± 0.290 (93%) | 0.742 | 0.012 | 0.984 | 0.001 |
| 2.5 × $10^{-8}$M ROH + $10^{-9}$M linoleoyl-DEA | 1.216 ± 0.131 (122%) | 0.001 | 0.002 | 0.896 | 0.030 |
| 2.5 × $10^{-6}$M ROH + $10^{-9}$M linoleoyl-DEA | 1.020 ± 0.220 (102%) | 0.751 | 0.777 | 0.054 | 0.001 |
| 2.5 × $10^{-9}$M ROH + $10^{-7}$M linoleoyl-DEA | 1.134 ± 0.175 (113%) | 0.016 | 0.069 | 0.321 | 0.067 |
| 2.5 × $10^{-9}$M ROH + $10^{-8}$M linoleoyl-DEA | 1.148 ± 0.101 (115%) | 0.002 | 0.011 | 0.284 | 0.016 | n = 9

Retinoic acid treatment acted as positive control and all concentrations of retinoic acid tested, i.e., 2.5×$10^{-7}$M, 2.5×$10^{-9}$M, significantly increased keratinocyte proliferation over both the ethanol control and each of the 2.5×$10^{-7}$M, 2.5×$10^{-8}$M, and 2.5×$10^{-9}$M, retinol treatments. Eight combinations of retinol and linoleoyl were examined with retinol concentrations of 2.5×$10^{-7}$M, 2.5×$10^{-8}$M, and 2.5×$10^{-9}$M, and linoleoyl-DEA concentrations of $10^{-16}$M, $10^{-7}$M $10^{-9}$M and $10^{-10}$M. The ratios of retinol:linoleoyl-DEA therefore ranged from 2000:1 to 1:500 as is illustrated in Table 7B.

TABLE 7B

Effect of Retinol and Linoleoyl-DEA on Keratinocyte Thymidine Incorporation

| w/w Ratio (ROH:lino) | Treatment | Increase |
|---|---|---|
| 2000:1 | 2.5 × $10^{-7}$M ROH + $10^{-10}$M linoleoyl-DEA | -7% |
| 200:1 | 2.5 × $10^{-7}$M ROH + $10^{-9}$M linoleoyl-DEA | +11%* |
| 26:1 | 2.5 × $10^{-8}$M ROH + $10^{-9}$M linoleoyl-DEA | +16%* |
| 2:1 | 2.5 × $10^{-7}$M ROH + $10^{-7}$M linoleoyl-DEA | +19%* |
| 1:5 | 2.5 × $10^{-7}$M ROH + $10^{-6}$M linoleoyl-DEA | +10%* |
| 1:5 | 2.5 × $10^{-9}$M ROH + $10^{-8}$M linoleoyl-DEA | +14%* |
| 1:50 | 2.5 × $10^{-9}$M ROH + $10^{-7}$M linoleoyl-DEA | +16%** |
| 1:500 | 2.5 × $10^{-9}$M ROH + $10^{-6}$M linoleoyl-DEA | +1% | n = 9
* = p < 0.05
** = p < 0.07

Increase indicated in Table 7B is equal to the % control thymidine incorporation of the ROH and linoleoyl-DEA treatment. Six of the eight combinations showed a synergistic increase in thymidine incorporation/soluble protein. The increased cell proliferation was statistically significant for five of these treatments at p <0.05 and for the other at p<0.07. The trend is clear—combinations of retinol and linoleoyl-DEA at ratios ranging from 200:1 through 1:50 synergistically increase keratinocyte cell proliferation.

The beneficial effect of combinations of retinol and fatty acid amide on keratinocytes was found to be derived from combinations where the ratio of retinol:fatty acid amide was between 200:1 to 1:50.

EXAMPLE 8

The Synergistic Inhibition of Keratinocyte Differentiation Induced By Retinyl Esters and Fatty Acid Amide is Most Effective at RE: Fatty Acid Amide Ratios ranging from 3500:1 to 1:300

In order to determine the range of retinyl palmitate:linoleoyl-DEA ratios which were most effective at enhancing the benefit of retinyl palmitate the effect on TGase after the addition of retinyl palmitate and linoleoyl-DEA in different ratios of amounts, was examined. These were compared to the effects of retinoic acid at several concentrations and the effects of retinyl palmitate and linoleoyl-DEA alone and the results are presented in Table 8A and 8B.

TABLE 8A

Effect of Retinyl Palmitate and Linoleoyl-DEA in Various ratios on Keratinocyte TGase.

| Treatment | mean TGase ± s.d (% contol) | p value vs Control | p value vs $10^{-n}$M RP | p value vs $10^{-n}$M RA | p value vs $10^{-n}$M lino'-DEA |
|---|---|---|---|---|---|
| Control | 0.218 ± 0.087 (100%) | — | — | — | — |
| 2.5 × $10^{-7}$M RA | 0.073 ± 0.022 (34%) | 0.001 | 0.001 | — | — |
| 2.5 × $10^{-8}$M RA | 0.138 ± 0.034 (64%) | 0.018 | 0.088 | — | — |
| 2.5 × $10^{-9}$M RA | 0.190 ± 0.091 (87%) | 0.448 | 0.383 | — | — |
| 2.5 × $10^{-6}$M Retinyl palmitate (RP) | 0.206 ± 0.034 (95%) | 0.662 | — | — | — |
| 2.5 × $10^{-7}$M Retinyl palmitate (RP) | 0.177 ± 0.026 (82%) | 0.633 | — | 0.001 | — |
| 2.5 × $10^{-8}$M Retinyl palmitate (RP) | 0.177 ± 0.054 (82%) | 0.870 | — | 0.088 | — |
| 2.5 × $10^{-9}$M Retinyl palmitate (RP) | 0.165 ± 0.030 (76%) | 0.919 | — | 0.383 | — |
| $10^{-6}$M linoleoyl-DEA | 0.186 ± 0.058 (87%) | 0.268 | — | — | — |
| $10^{-7}$M linoleoyl-DEA | 0.175 ± 0.059 (80%) | 0.136 | — | — | — |
| $10^{-8}$M linoleoyl-DEA | 0.188 ± 0.046 (86%) | 0.284 | — | — | — |
| $10^{-9}$M linoleoyl-DEA | 0.185 ± 0.031 (85%) | 0.227 | — | — | — |
| 2.5 × $10^{-6}$M RP + $10^{-6}$M linoleoyl-DEA | 0.086 ± 0.012 (40%) | 0.001 | 0.001 | 0.001 | 0.001 |

TABLE 8A-continued

Effect of Retinyl Palmitate and Linoleoyl-DEA in
Various ratios on Keratinocyte TGase.

| Treatment | mean TGase ± s.d (% contol) | p value vs Control | p value vs $10^{-n}$M RP | p value vs $10^{-n}$M RA | p value vs $10^{-n}$M lino'-DEA |
|---|---|---|---|---|---|
| $2.5 \times 10^{-6}$M RP + $10^{-7}$M linoleoyl-DEA | 0.094 ± 0.037 (43%) | 0.001 | 0.001 | 0.001 | 0.001 |
| $2.5 \times 10^{-6}$M RP + $10^{-8}$M linoleoyl-DEA | 0.092 ± 0.020 (42%) | 0.001 | 0.001 | 0.001 | 0.001 |
| $2.5 \times 10^{-6}$M RP + $10^{-9}$M linoleoyl-DEA | 0.110 ± 0.028 (50%) | 0.001 | 0.001 | 0.001 | 0.001 |
| $2.5 \times 10^{-7}$M RP + $10^{-6}$M linoleoyl-DEA | 0.046 ± 0.013 (21%) | 0.001 | 0.001 | 0.003 | 0.001 |
| $2.5 \times 10^{-7}$M RP + $10^{-7}$M linoleoyl-DEA | 0.093 ± 0.033 (43%) | 0.001 | 0.001 | 0.147 | 0.001 |
| $2.5 \times 10^{-7}$M RP + $10^{-8}$M linoleoyl-DEA | 0.112 ± 0.022 (52%) | 0.001 | 0.001 | 0.001 | 0.001 |
| $2.5 \times 10^{-7}$M RP + $10^{-9}$M linoleoyl-DEA | 0.133 ± 0.017 (61%) | 0.002 | 0.001 | 0.001 | 0.001 |
| $2.5 \times 10^{-8}$M RP + $10^{-6}$M linoleoyl-DEA | 0.069 ± 0.034 (32%) | 0.001 | 0.001 | 0.001 | 0.001 |
| $2.5 \times 10^{-8}$M RP + $10^{-7}$M linaleoyl-DEA | 0.103 ± 0.053 (47%) | 0.001 | 0.003 | 0.113 | 0.005 |
| $2.5 \times 10^{-8}$M RP + $10^{-8}$M linoleoyl-DEA | 0.112 ± 0.066 (52%) | 0.001 | 0.015 | 0.319 | 0.004 |
| $2.5 \times 10^{-8}$M RP + $10^{-9}$M linoleoyl-DEA | 0.073 ± 0.030 (33%) | 0.001 | 0.001 | 0.001 | 0.001 |
| $2.5 \times 10^{-9}$M RP + $10^{-6}$M linoleoyl-DEA | 0.092 ± 0.021 (42%) | 0.001 | 0.001 | 0.011 | 0.001 |
| $2.5 \times 10^{-9}$M RP + $10^{-9}$M linoleoyl-DEA | 0.128 ± 0.039 (59%) | 0.009 | 0.026 | 0.098 | 0.002 | n = 3

TABLE 8B

Effect of Retinyl Palmitate and Linoleoyl-DEA in
Various Ratios on Keratinocyte TGase

| Treatment | mean TGase ± s.d (% control) | p value vs Control | p value vs $10^{-n}$M RP | p value vs $10^{-n}$M RA | p value vs $10^{-n}$M lino'-DEA |
|---|---|---|---|---|---|
| Control | 0.122 ± 0.033 (100%) | — | 0.001 | 0.001 | — |
| $2.5 \times 10^{-7}$M RA | 0.015 ± 0.025 (12%) | 0.001 | 0.001 | — | — |
| $2.5 \times 10^{-6}$M Retinyl palmitote (RP) | 0.063 ± 0.019 (52%) | 0.001 | — | 0.001 | — |
| $2.5 \times 10^{-10}$M Retinyl palmitate (RP) | 0.132 ± 0.038 (108%) | 0.504 | — | 0.001 | — |
| $10^{-10}$M linoleoyl-DEA | 0.080 ± 0.030 (66%) | 0.001 | — | — | — |
| $10^{-6}$M linoleoyl-DEA | 0.037 ± 0.008 (37%) | 0.007 | — | — | — |
| $2.5 \times 10^{-9}$M RP + $10^{-6}$M linoleoyl-DEA | 0.056 ± 0.018 (44%) | 0.001 | 0.001 | 0.003 | 0.029 |
| $2.5 \times 10^{-9}$M RP + $10^{-10}$M linoleoyl-DEA | 0.086 ± 0.026 (70%) | 0.014 | 0.001 | 0.001 | 0.707 | n = 3

Retinoic acid treatment acted as positive control and all concentrations of retinoic acid tested, i.e., $2.5 \times 10^{-7}$M, $2.5 \times 10^{-8}$M and $2.5 \times 10^{-9}$M, significantly decreased keratinocyte TGase levels compared to both the ethanol control and each of the $2.5 \times 10^{-7}$M, $2.5 \times 10^{-8}$M and $2.5 \times 10^{-9}$M retinyl palmitate treatments. Sixteen combinations of retinyl palmitate and linoleoyl-DEA were examined with retinyl palmitate concentrations of $2.5 \times 10^{-6}$M, $2.5 \times 10^{-7}$M, $2.5 \times 10^{-8}$M, $2.5 \times 10^{-9}$M and $2.5 \times 10^{-10}$M and linoleoyl-DEA concentrations of $10^{-6}$M, $10^{-7}$M, $10^{-8}$M, $10^{-9}$M and $10^{-10}$M. The w/w ratios of retinyl palmitate:linoleoyl-DEA therefore ranged from 35000:1 to 1:3000 as is illustrated in Table 8C.

TABLE 8C

The Effective Ratios of Retinyl Palmitate and
Linoleoyl-DEA on Inhibition of Keratinocyte TGase

| w/w Ratio (RP:lino) | Treatment | Synergistic decrease (over RP + lino'-DEA) |
|---|---|---|
| 35000:1 | $2.5 \times 10^{-6}$M RP + $10^{-10}$M linoleoyl-DEA | 0% |
| 3500:1 | $2.5 \times 10^{-6}$M RP + $10^{-9}$M linoleoyl-DEA | 27%* |
| 350:1 | $2.5 \times 10^{-6}$M RP + $10^{-8}$M linoleoyl-DEA | 40%* |
| 350:1 | $2.5 \times 10^{-7}$M RP + $10^{-9}$M linoleoyl-DEA | 5%* |
| 35:1 | $2.5 \times 10^{-6}$M RP + $10^{-7}$M linoleoyl-DEA | 32%* |
| 35:1 | $2.5 \times 10^{-7}$M RP + $10^{-8}$M linoleoyl-DEA | 16%* |
| 35:1 | $2.5 \times 10^{-8}$M RP + $10^{-9}$M linoleoyl-DEA | 33%* |
| 3.5:1 | $2.5 \times 10^{-6}$M RP + $10^{-6}$M linoleoyl-DEA | 41%* |
| 3.5:1 | $2.5 \times 10^{-7}$M RP + $10^{-7}$M linoleoyl-DEA | 19%* |
| 3.5:1 | $2.5 \times 10^{-8}$M RP + $10^{-8}$M linoleoyl-DEA | 16%* |
| 3.5:1 | $2.5 \times 10^{-9}$M RP + $10^{-9}$M linoleoyl-DEA | 2%* |
| 1:3 | $2.5 \times 10^{-7}$M RP + $10^{-6}$M linoleoyl-DEA | 46%* |
| 1:3 | $2.5 \times 10^{-8}$M RP + $10^{-7}$M linoleoyl-DEA | 15%* |
| 1:30 | $2.5 \times 10^{-8}$M RP + $10^{-6}$M linoleoyl-DEA | 35%* |
| 1:300 | $2.5 \times 10^{-9}$M RP + $10^{-6}$M linoleoyl-DEA | 19%* |
| 1:3000 | $2.5 \times 10^{-10}$M RP + $10^{-6}$M linoleoyl-DEA | 0% | n = 9
* = $p < 0.05$

The synergistic decrease indicated in Table 8C is equal to the difference between the % control TGase of the retinyl palmitate+linoleoyl-DEA treatment and the combined decreases of the individual retinyl palmitate and linoleoyl-DEA treatment. Fourteen of the combinations showed a synergistic decrease in TGase levels. The decreased TGase in these fourteen combinations was statistically significant.

The trend is clear—combinations of retinyl palmitate and linoleoyl-DEA at ratios ranging from 3500:1 through 1:300 synergistically decrease keratinocyte differentiation.

Examples 1–8 demonstrate that retinoic acid, in a dose dependent manner, increased thymidine incorporation and decreased transglutaminase I levels in skin keratinocytes. In other words retinoic acid increased keratinocyte proliferation and decreased keratinocyte differentiation. In Examples 1–8, retinoic acid was used as positive control and reference compound against which the other compounds under analysis were compared. Retinol was significantly less effective than retinoic acid at inhibiting keratinocyte differentiation and completely ineffective at increasing keratinocyte proliferation.

The unexpected results of Examples 1–8, however, was that the effect of retinol on cultured keratinocytes can be enhanced to levels approaching those of retinoic acid by combining retinol or retinyl ester with a fatty acid amide—a compound which exerts little or no benefit on its own. The results documented above demonstrate that certain longer chain fatty acid amides act synergistically with retinol or retinyl ester, both to increase keratinocyte proliferation and to decrease keratinocyte differentiation, mimicking the effect of retinoic acid.

The potentiation of the benefit of retinol or retinyl esters on keratinocytes was restricted to the fatty acid amide. Neither the free fatty acid nor the fatty acid ester in combination with retinol had a synergistic benefit.

The beneficial effect of combinations of retinol and fatty acid amide on keratinocytes was found to be derived from combinations where the ratio of retinol:fatty acid amide was between 200:1 to 1:50. Similarly, the effective ratios of retinyl ester:fatty acid amide was found to be between 3500:1 and 1:300.

EXAMPLE 9

This example illustrates a high internal phase water-in-oil emulsion incorporating the inventive composition.

| | % w/w |
|---|---|
| Retinol | 0.5 |
| Fully hydrogenated coconut oil | 3.9 |
| Linoleoyl-diethanolamide | 5 |
| Brij 92* | 5 |
| Bentone 38 | 0.5 |
| $MgSO_4 7H_2O$ | 0.3 |
| Butylated hydroxy toluene | 0.01 |
| Perfume | qs |
| Water | to 100 |

*Brij 92 is polyoxyethylene (2) oleyl ether

EXAMPLE 10

This example illustrates an oil-in-water cream incorporating the inventive composition.

| | % w/w |
|---|---|
| Retinol | 0.15 |
| Mineral oil | 4 |
| Cocoyl diethanolamide | 1 |
| Brij 56* | 4 |
| Alfol 16RD* | 4 |
| Triethanolamine | 0.75 |
| Butane-1,3-diol | 3 |
| Xahthan gum | 0.3 |
| Perfume | qs |
| Butylated hydroxy toluene | 0.01 |
| Water | to 100 |

*Brij 56 is cetyl alcohol POE (10)
Alfol 16RD is cetyl alcohol

EXAMPLE 11

This example illustrates an alcoholic lotion incorporating the composition according to the invention.

| | % w/w |
|---|---|
| Retinyl palmitate | 0.15 |
| Linoleoyl monoethanolamide | 0.1 |
| Ethanol | 40 |
| Perfume | qs |
| Butylated hydroxy toluene | 0.01 |
| Water | to 100 |

EXAMPLE 12

This example illustrates another alcoholic lotion containing the inventive composition.

| | % w/w |
|---|---|
| Retinol | 0.15 |
| Palmitoyl-monoethanolamide | 0.1 |
| Ethanol | 40 |
| Antioxidant | 0.1 |
| Perfume | qs |
| Water | to 100 |

EXAMPLE 13

This example illustrates a suncare cream incorporating the composition of the invention:

| | % w/w |
|---|---|
| Retinol | 0.01 |
| Linoleoyl monoethanolamide | 0.1 |
| Silicone oil 200 cts | 7.5 |
| Glycerylmonostearate | 3 |
| Cetosteryl alcohol | 1.6 |
| Polyoxyethylene-(20)-cetyl alcohol | 1.4 |
| Xanthan gum | 0.5 |
| Parsol 1789 | 1.5 |
| Octyl methoxycinnate (PARSOL MCX) | 7 |
| Perfume | qs |
| Color | qs |
| Water | to 100 |

EXAMPLE 14

This example illustrates a non-aqueous skin care composition incorporating the inventive combination.

| | % w/w |
|---|---|
| Retinyl palmitate | 0.15 |
| Linoleoyl diethanolamide | 1 |

-continued

|  | % w/w |
|---|---|
| Silicone gum SE-30[1] | 10 |
| Silicone fluid 345[2] | 20 |
| Silicone fluid 344[3] | 55.79 |
| Squalene | 10 |
| Linoleic acid | 0.01 |
| Cholesterol | 0.03 |
| 2-hydroxy-n-octanoic acid | 0.7 |
| Vitamin E linoleate | 0.5 |
| Herbal oil | 0.5 |
| Ethanol | 2 |

[1] A dimethyl silicone polymer having a molecular weight of at least 50,000 and a viscosity of at least 10,000 centistokes at 25° C., available from GEC
[2] Dimethyl siloxane cyclic pentamer, available from Dow Corning Corp.
[3] Dimethyl siloxane tetramer, available from DOW Corning Corp.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A skin conditioning composition comprising
   (a) from about 0.001% to about 10% of a compound selected from the group consisting of retinol and a retinyl ester;
   (b) from about 0.0001% to about 50% of a fatty acid amide wherein the fatty acid contains from 8 to 24 carbon atoms, wherein the amide is selected from the group consisting of, unsubstituted amide, N-alkylamide, N,N-dialkylamide, N-alkanolamide, N,N-dialkanolamide and mixtures thereof; and
   (c) a cosmetically acceptable vehicle; wherein the ratio of retinol to the fatty acid amide is in the range of from about 200:1 to about 1:50 and wherein the ratio of the retinyl ester to the fatty acid amide is in the range of from 3,500:1 to 1:300.

2. The composition of claim 1 wherein the fatty acid is an essential fatty acid.

3. The composition of claim 1 wherein the N-alkanolamide is N-ethanolamide.

4. The composition of claim 1 wherein the N,N-dialkanolamide is N,N-diethanolamide.

5. The composition of claim 1 wherein the retinyl ester is selected from the group consisting of retinyl palmitate, retinyl acetate and retinyl propionate, and mixtures thereof.

6. The composition of claim 1 wherein ingredient (a) is retinol.

7. The composition of claim 1 wherein ingredient (a) is a retinyl ester.

8. A method of conditioning skin the method comprising applying topically to skin the composition of claim 1.

9. A method of mimicking the effect on skin of retinoic acid, the method comprising applying to the skin the composition of claim 1.

* * * * *